United States Patent [19]

Hernday et al.

[11] Patent Number: 5,033,846
[45] Date of Patent: Jul. 23, 1991

[54] LIGHTWAVE COMPONENT ANALYZER FOR DETERMINATION OF CHROMATIC DISPERSION IN SINGLE MODE OPTICAL FIBER

[75] Inventors: Paul R. Hernday; Roger W. Wong, both of Santa Rosa; Harry Chou, Windsor, all of Calif.

[73] Assignee: Hewlett-Packard Company, Palo Alto, Calif.

[21] Appl. No.: 468,437

[22] Filed: Jan. 22, 1990

[51] Int. Cl.$^5$ .............................................. G01N 21/84
[52] U.S. Cl. .................................................. 356/73.1
[58] Field of Search ........................................ 356/73.1

[56] References Cited

FOREIGN PATENT DOCUMENTS

53-20349 2/1978 Japan .................................... 356/73.1

*Primary Examiner*—Vincent P. McGraw
*Attorney, Agent, or Firm*—William C. Milks, III

[57] ABSTRACT

A lightwave component analyzer and method for determining chromatic dispersion in single mode optical fiber. The lightwave component analyzer initially performs various measurements that are used in the determination of chromatic dispersion in single mode optical fiber. The lightwave component analyzer then computes a chromatic dispersion factor using the measured parameters, as well as additional parameters which are stored in the analyzer or entered by a user. Various expressions are described for computation of chromatic dispersion in single mode optical fiber.

20 Claims, 6 Drawing Sheets

SEMI-AUTOMATIC MEASUREMENT OF FIBER DISPERSION

FIG 6 form of the method in accordance with the invention for determining chromatic dispersion in a single mode optical fiber using the fiber length;

LIGHTWAVE COMPONENT ANALYZER FOR DETERMINATION OF CHROMATIC DISPERSION IN SINGLE MODE OPTICAL FIBER

BACKGROUND OF THE INVENTION

This invention relates to electronic instruments for measuring various optical characteristics of optical, opto-electrical, and electro-optical systems, subsystems, and components, and preferably electrical characteristics, as well, and, more particularly, to instrumentation for measuring optical characteristics of optical fiber utilized in such systems, subsystems, and components. Specifically, one embodiment of the invention is directed to providing a determination of chromatic dispersion in single mode optical fiber.

Single mode optical fiber exhibits what is generally referred to as "chromatic dispersion." Chromatic dispersion is characterized by the phenomenon that optical signals having different wavelengths travel along a single mode optical fiber at different speeds.

For example, light sources, such as lasers utilized in optical communications systems, typically produce optical signals which have some inherent or modulation-induced spectral width, which results in optical signal components having different wavelengths. The effect of a chromatically dispersive single mode optical fiber on such modulation-induced optical signal components, for example, is to re-arrange the phase relationships of the modulation components, producing a distorted optical signal at the receiving end of the fiber.

Unfortunately, high-rate optical receivers in optical communications systems are particularly vulnerable to chromatic dispersion. The distinction between adjacent pulses is degraded, and the "decision," or detection, process for pulse-coded data becomes less certain.

Since experiments with spooled or deployed single mode optical fiber can be dramatically influenced by effects of chromatic dispersion, optical communications system, subsystem, and component designers must be aware of the dispersion factor at the operating, or carrier, wavelength. Accordingly, there is a particular need to determine chromatic dispersion in single mode optical fiber so that this fiber can be characterized and so that receivers in optical communications systems can be designed effectively.

SUMMARY OF THE INVENTION

One embodiment of the present invention provides a lightwave component analyzer and method for determining chromatic dispersion in single mode optical fiber. The lightwave component analyzer initially performs various measurements that are used in the determination of chromatic dispersion in single mode optical fiber. The lightwave component analyzer then computes a chromatic dispersion factor using the measured parameters, as well as additional parameters which are stored in the analyzer or entered by a user. Various expressions have been derived for computation of chromatic dispersion in single mode optical fiber, which are solved using the measured and entered parameters to provide the chromatic dispersion factor. Preferably, chromatic dispersion is determined utilizing an optical source which produces an optical carrier signal having a wavelength of 1550 nm.

In one embodiment of the invention, the free-space wavelength of the optical carrier signal is known and is entered by a user. Also, the length of the single mode optical fiber is known and is entered by the user or, alternatively, can be measured by the lightwave component analyzer. The lightwave component analyzer then measures the modulating frequency, $F_m$, at the minima, or nulls, of the AM frequency response characteristic of the single mode optical fiber in Hz. A marker is preferably placed at the first minimum, or null. Using the entered free-space wavelength of the optical carrier signal, the single mode fiber length, and the modulating frequency at the first minimum, or null, in the AM frequency response measurement, the lightwave component analyzer computes a chromatic dispersion factor in ps/nm/km.

In another embodiment of the invention, the index of refraction and the free-space wavelength are known and are entered by the user. Also, the travel time of an optical signal in the single mode optical fiber is known and is entered by the user or, alternatively, is measured by the lightwave component analyzer. Travel time is preferably measured in advance using an inverse Fourier transformation process resident in the lightwave component analyzer, which converts data measured in the frequency domain to the time domain. The lightwave component analyzer then measures $F_m$. A marker is preferably placed at the first minimum, or null, in the AM frequency response characteristic of the single mode optical fiber. Using the entered index of refraction, the travel time in the single mode optical fiber, and the modulating frequency at the first minimum, or null, in the AM frequency response measurement, the lightwave component analyzer computes a chromatic dispersion factor.

Improvement in the accuracy of chromatic dispersion measurements can be obtained by measuring the frequency of the minima, or nulls, twice, once with the optical modulator that modulates the optical carrier signal biased at quadrature on a positive slope and again with the modulator biased at quadrature on a negative slope, and then using the average of these null measurements to compute the chromatic dispersion factor. This cancels the effect of unwanted phase modulation.

BRIEF DESCRIPTION OF THE DRAWINGS

The above and other features of the invention and the concomitant advantages will be better understood and appreciated by persons skilled in the field to which the invention pertains in view of the following description given in conjunction with the accompanying drawings. In the drawings:

FIG. 1, comprising

DETAILED DESCRIPTION OF THE PREFERRED EMBODIMENTS

Figure 1A:
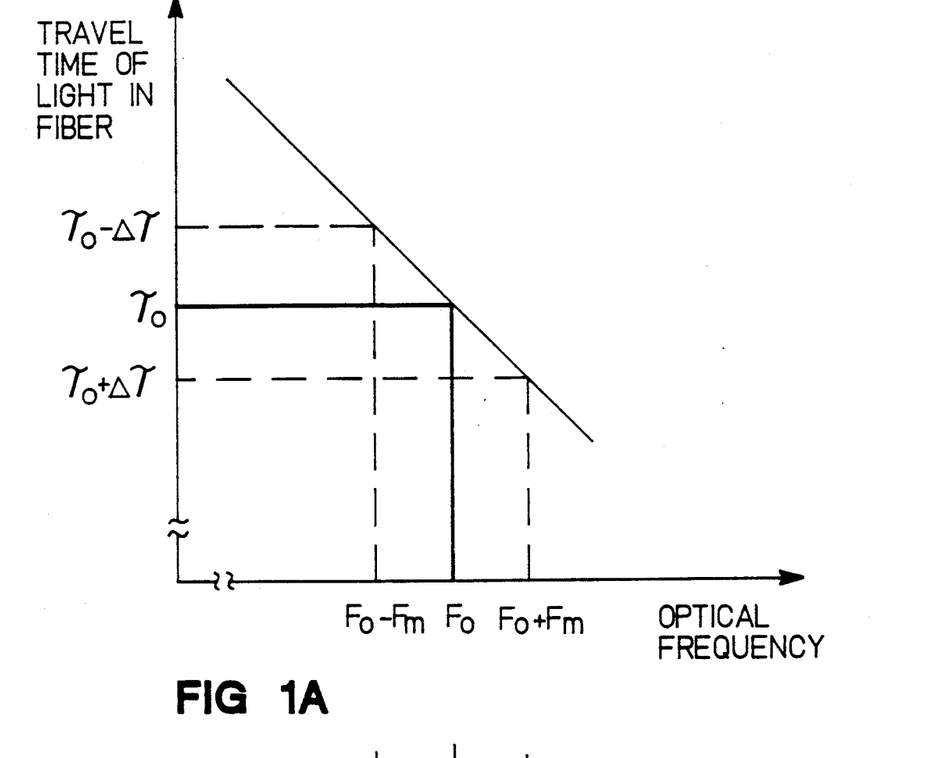
FIGS. 1A and 1B, illustrates optical signal delay in a single mode optical fiber as a function of frequency (FIG. 1A) and the corresponding frequency spectrum of the propagating optical signals (FIG. 1B)
Figure 1B:
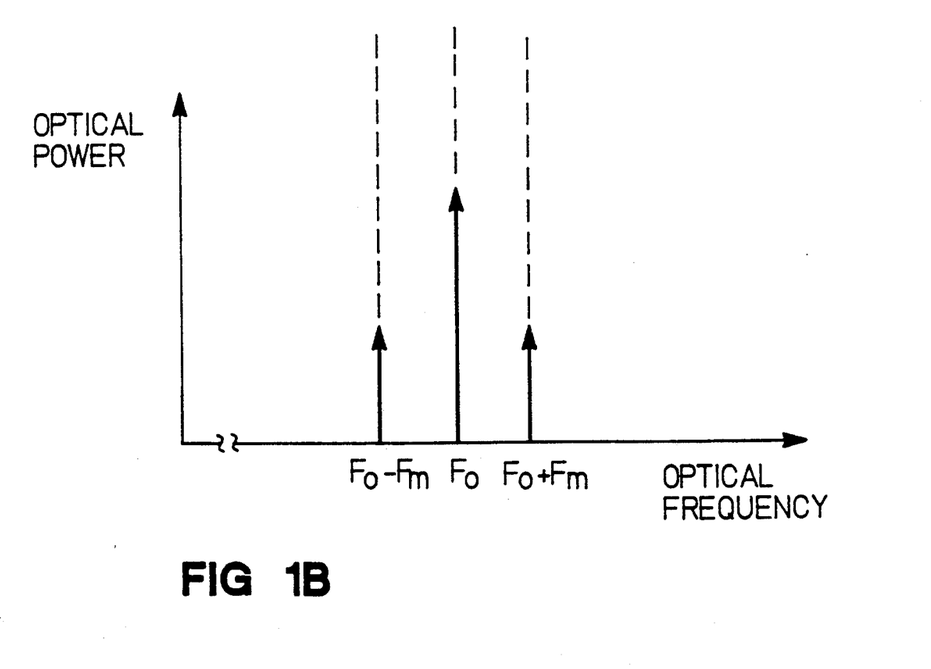

FIG. 1A illustrates the optical signal delay as a function of frequency in a single mode optical fiber for optical signals having the frequency spectrum shown in FIG. 1B. As illustrated in FIG. 1A, the optical signal delay typically decreases with increasing frequency.

At a frequency $F_o$ of an optical carrier signal, an optical signal delay, $\tau_o$, is a given value. However, when the optical carrier signal is modulated, the modulated optical carrier signal has sidebands at modulation frequencies $F_o$ minus $F_m$ and $F_o$ plus $F_m$. These modulation frequencies are differentially delayed in the single mode optical fiber, that is, they experience optical delays $\tau_{Fo-Fm}$ and $\tau_{Fo+Fm}$, which are respectively greater than and less than the delay $T_o$.

Now, consider a length L of single mode optical fiber, which exhibits chromatic dispersion, fed by an ideal laser having a single spectral line of zero linewidth. Suppose that the optical carrier signal produced by the laser is ideally intensity modulated in the small signal regime and that no chirp is created. The resultant modulated optical signal can be represented in the frequency domain by a spectrum consisting of the CW optical source signal and a pair of AM sidebands with one sideband spaced above and the other sideband spaced below the CW signal by the modulation frequency.

As the modulation rate is changed, a frequency can be reached at which fiber chromatic dispersion causes the phase of the lower sideband to be advanced by 90 degrees and the phase of the upper sideband to be retarded by 90 degrees. Under this condition, the modulation phasors corresponding to the propagating modulation sidebands add in such a way as to cancel the AM component.

Accordingly, a minimum will be observed in the AM frequency response of the single mode optical fiber. Additional minima will occur at modulation frequencies at which sideband phase is advanced and retarded by 270 degrees, 450 degrees, and so on, that is, at 180-degree intervals beyond the initial 90-degree phase shift.

A simple expression of this relationship is given below:

$$F_m = F_o \sqrt{\frac{(1 + 2N)}{2DLc}} \quad (1)$$

The variables in expression (1) are given below with their associated measurement units:

D dispersion constant, s/m/m;
$F_o$ optical frequency of the unmodulated optical source signal, Hz;
$F_m$ measured modulating frequency at the minima, Hz;
c speed of light in free-space, m/s;
L length of single mode optical fiber, m; and
N integer 0,1,2,3 . . . corresponding to observed minima in AM modulation frequency response of fiber.

At each value of N, the single mode optical fiber will exhibit a minimum in its AM modulation frequency response.

The above expression (1) can be solved for the dispersion constant, D, at the first null (N=0) as follows:

$$D_{N=0} = \frac{c}{2L\lambda_o^2 F_m^2} \quad (2)$$

where $\lambda_o$ is the free-space wavelength of the optical signal produced by the optical source in meters and is equal to $c/F_o$. If the length of the single mode optical fiber is not known, the fiber length can be measured using an HP 8703A lightwave component analyzer manufactured by the Network Measurements Division of Hewlett-Packard Company, Santa Rosa, Calif., as will be described later.

Also, expression (2) can be modified to eliminate the need for knowledge of the length of the single mode optical fiber. The travel time of light in the single mode optical fiber, $\tau_o$, at the wavelength $\lambda_o$ of the optical source can be measured using the time domain feature of the HP 8703A lightwave component analyzer, as will be described later.

With knowledge of n, $\lambda_o$, and $\tau_o$, expression (2) can be rewritten as follows:

$$D_{N=0} = \frac{n}{2\lambda_o^2 F_m^2 \tau_o} \quad (3)$$

Previously unidentified variables in expression (3) are given below with their measurement units:

n index of refraction of the glass single mode optical fiber core at the frequency $F_o$, dimensionless; and
$\tau_o$ time required for light at frequency $F_o$ to travel the length of the fiber, s.

A method for determining chromatic dispersion for a single mode optical fiber can be incorporated into the HP 8703A lightwave component analyzer for the purpose of providing an added instrument capability that is accessible during measurements on optical, opto-electrical, and electro-optical systems, subsystems, and components. Accordingly, the HP 8703A can be configured to provide a computation, or indirect measurement, of chromatic dispersion in a single mode optical fiber at the particular wavelength of the lightwave component analyzer which, for example, can incorporate a 1550 nm distributed feedback (DFB) laser as an optical source.

Considered in more detail, the HP 8703A lightwave component analyzer is disclosed in a co-pending patent application Ser. No. 07/390,570, filed on Aug. 7, 1989, in the names of Paul R. Hernday, Roger W. Wong, and Hugo Vifian, entitled "LIGHTWAVE COMPONENT ANALYZER," and assigned to Hewlett-Packard Company. The 0.13 to 20 GHz range of the HP 8703A lightwave component analyzer enables this instrument to reach the first AM frequency response minimum of a realistic length sample of single mode optical fiber. A DFB laser operating at 1550 nm preferably provides the narrow spectral width, single lasing line optical signal needed to allow development of at least one deep, precise minimum in the AM frequency response characteristic of the single mode optical fiber being measured. Indirect modulation of the laser via a Mach Zehnder interferometer incorporated into the HP 8703A lightwave component analyzer produces clean, chirp-free sinusoidal modulation. An optical isolator incorporated into the HP 8703A lightwave component analyzer between the laser and the modulator preserves excellent spectral quality of the laser. A time domain feature allows precise measurement of the time of travel of light in the single mode optical fiber being measured. The convenient user interface, involving a firmware-generated menu and soft keys, allows easy access to the capability for determining chromatic dispersion.

In accordance with various embodiments of the invention, a lightwave component analyzer, such as the HP 8703A, is provided with a partially automated or a primarily manual chromatic dispersion determination feature. The determination of chromatic dispersion can be based on utilizing either expression (2) or expression (3), above.

Figure 2:
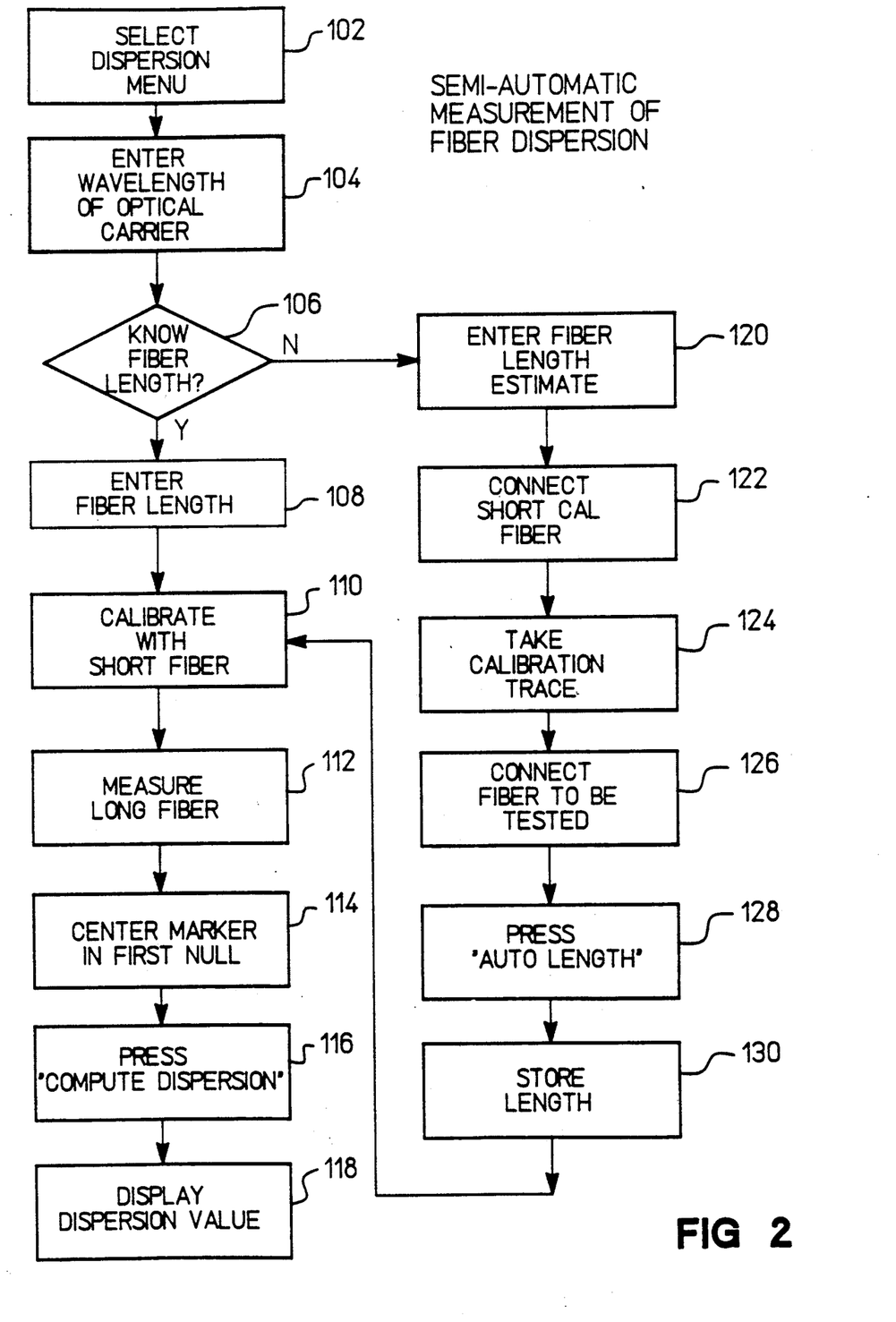
FIG. 2 is a flow chart of one embodiment of the method in accordance with the invention for determining chromatic dispersion in a single mode optical fiber using the fiber length.

Considered in more detail, one embodiment of the partially automated chromatic dispersion method in accordance with the invention is shown in FIG. 2. As shown in FIG. 2, in the case of partially automated chromatic dispersion determination based on expression (2), above, the chromatic dispersion function of the lightwave component analyzer is initially selected by the user, and this function of the lightwave component analyzer is activated, as indicated by the numeral 102 shown in FIG. 2. Next, as indicated by the numeral 104 shown in FIG. 2, the lightwave component analyzer prompts the user to enter the known free-space wavelength, $\lambda_o$, of the optical signal produced by the optical source in meters. Then, the lightwave component analyzer queries the user whether or not he or she knows the length of the single mode optical fiber, as indicated by the numeral 106 shown in FIG. 2.

If the length of the single mode optical fiber is known, that is, the length has been previously measured or provided by the manufacturer of the fiber, then the user responds to the query at step 106 shown in FIG. 2 by entering the fiber length, as indicated by the numeral 108 shown in FIG. 2. The user next preferably connects a calibration standard in the form of a short length of single mode optical fiber to the lightwave component analyzer, as indicated by the numeral 110 shown in FIG. 2, and the lightwave component analyzer performs a calibration measurement utilizing the short fiber. Then, the user disconnects the short single mode optical fiber calibration standard from the lightwave component analyzer and connects the single mode optical fiber to be measured, so that its chromatic dispersion factor can be determined, and the lightwave component analyzer is used to measure $F_m$, as indicated by the numeral 112 shown in FIG. 2.

Next, the user preferably centers a marker of the lightwave component analyzer in the first minimum, or null, observed on the AM frequency response characteristic of the single mode optical fiber displayed by the lightwave component analyzer, as indicated by the numeral 114 shown in FIG. 2. Then, the user actuates a "COMPUTE DISPERSION" key, which can be a dedicated instrument key or a firmware-generated menu and soft key displayed to the user, as indicated by the numeral 116 shown in FIG. 2. Finally, the lightwave component analyzer computes the chromatic dispersion factor D in ps/nm/km in accordance with expression (2), above, using 1) the speed of light in free-space, c, resident in the memory of the lightwave component analyzer, 2) the entered free-space wavelength $\lambda_o$ of the optical carrier signal, 3) the entered length L of the single mode optical fiber, and 4) the measured modulating frequency $F_m$ at the first minimum in the AM frequency response characteristic of the fiber, as indicated by the numeral 118 shown in FIG. 2.

If, on the other hand, the user responds at step 106 shown in FIG. 2 that the length of the single mode optical fiber is not known, the lightwave component analyzer preferably prompts the user to enter an estimate of the length of the fiber to enable the lightwave component analyzer to select an appropriate frequency range for calibration, as indicated by the numeral 120 shown in FIG. 2. Then, the user preferably connects a calibration standard in the form of a short length of single mode optical fiber to the lightwave component analyzer, as indicated by the numeral 122 shown in FIG. 2. Next, the lightwave component analyzer performs a calibration measurement utilizing the short single mode optical fiber as a calibration standard, as indicated by the numeral 124 shown in FIG. 2. Then, the user disconnects the short single mode optical fiber calibration standard from the lightwave component analyzer and connects the single mode optical fiber to be measured, as indicated by the numeral 126 shown in FIG. 2. The user next actuates a "AUTO LENGTH" key, which can be a dedicated instrument key or a firmware-generated menu and soft key displayed to the user, as indicated by the numeral 128 shown in FIG. 2. Then, the lightwave component analyzer measures and stores the length of the single mode optical fiber being measured so that its chromatic dispersion factor can be determined, as indicated by the numeral 130 shown in FIG. 2. The length determination method is resident in the commercially available HP 8703A lightwave component analyzer and does not form part of this invention.

After the lightwave component analyzer determines the length of the single mode optical fiber whose chromatic dispersion is to be determined, the user preferably disconnects the length of the single mode optical fiber whose chromatic dispersion is to be determined and preferably reconnects the calibration standard in the form of the short length of single mode optical fiber to the lightwave component analyzer, in accordance with the step 110 shown in FIG. 2. Then, the lightwave component analyzer performs a calibration measurement utilizing the short single mode optical fiber, which is followed by the steps 112, 114, 116, and 118 shown in FIG. 2 to produce a computation of the chromatic dispersion factor D for the fiber in ps/nm/km in accordance with expression (2), above.

Figure 3:
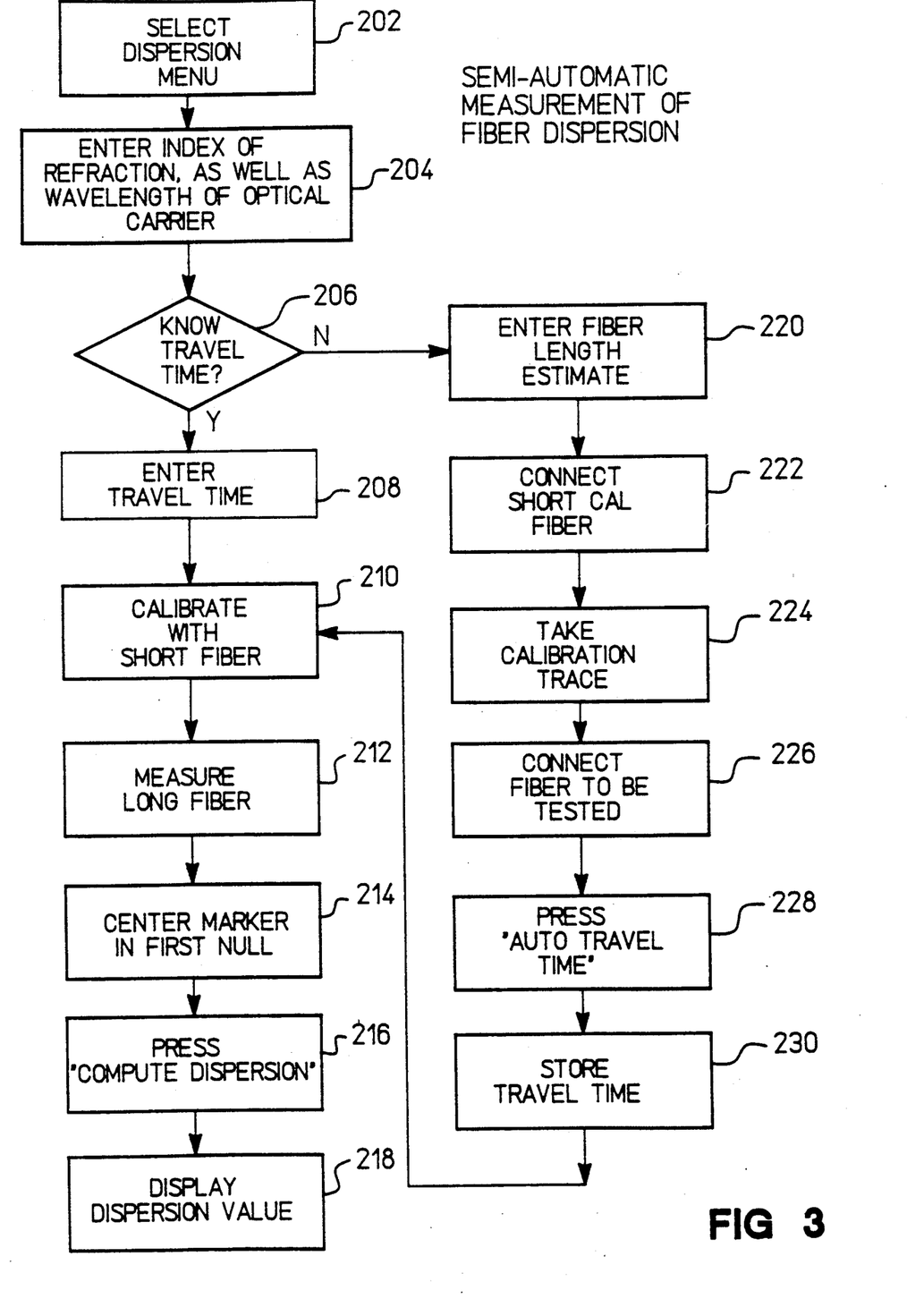
FIG. 3 is a flow chart of another embodiment of the method in accordance with the invention for determining chromatic dispersion in a single mode optical fiber using optical signal travel time in the fiber.

Another embodiment of the partially automated chromatic dispersion method in accordance with the invention is shown in FIG. 3. As shown in FIG. 3, in the case of partially automated chromatic dispersion determination based on expression (3), above, the chromatic dispersion function of the lightwave component analyzer is initially selected by the user, and this function of the lightwave component analyzer is activated, as indicated by the numeral 202 shown in FIG. 3. Next, as indicated by the numeral 204 shown in FIG. 3, the lightwave component analyzer prompts the user to enter the known index of refraction of the single mode optical fiber at the frequency $F_o$ of the optical signal produced by the optical source, as well as the free-space wavelength, $\lambda_o$, of the optical signal produced by the optical source. Then, the lightwave component analyzer queries the user whether or not he or she knows the time in seconds required for light at the frequency $F_o$ to travel the length of the single mode optical fiber, as indicated by the numeral 206 shown in FIG. 3.

If the travel time in the single mode optical fiber is known, that is, the travel time has been previously measured, then the user responds to the query at step 206 shown in FIG. 3 by entering the travel time, as indicated by the numeral 208 shown in FIG. 3. The user next preferably connects a calibration standard in the form of a short length of single mode optical fiber to the lightwave component analyzer, as indicated by the numeral 210 shown in FIG. 3, and the lightwave component analyzer performs a calibration measurement utilizing the short fiber. Then, the user disconnects the short single mode optical fiber calibration standard from the lightwave component analyzer and connects the single mode optical fiber to be measured, so that its chromatic dispersion factor can be determined, and the lightwave component analyzer is used to measure $F_m$, as indicated by the numeral 212 shown in FIG. 3.

Next, the user preferably centers a marker of the lightwave component analyzer in the first minimum, or null, observed on the AM frequency response characteristic of the single mode optical fiber displayed by the lightwave component analyzer, as indicated by the numeral 214 shown in FIG. 3. Then, the user actuates a "COMPUTE DISPERSION" key, which can be a dedicated instrument key or a firmware-generated menu and soft key displayed to the user, as indicated by the numeral 216 shown in FIG. 3. Finally, the lightwave component analyzer computes the chromatic dispersion factor D in ps/nm/km in accordance with expression (3), above, using 1) the entered index of refraction n, 2) the entered free-space wavelength $\lambda_o$ of the optical carrier signal, 3) the entered travel time of light in the single mode optical fiber, and 4) the measured modulating frequency $F_m$ at the first minimum in the AM frequency response characteristic of the fiber, as indicated by the numeral 218 shown in FIG. 3.

If, on the other hand, the user responds at step 206 shown in FIG. 3 that the travel time in the single mode optical fiber is not known, the lightwave component analyzer preferably prompts the user to enter an estimate of the length of the fiber to enable the lightwave component analyzer to select an appropriate frequency range for calibration, as indicated by the numeral 220 shown in FIG. 3. Then, the user preferably connects a calibration standard in the form of a short length of single mode optical fiber to the lightwave component analyzer, as indicated by the numeral 222 shown in FIG. 3. Next, the lightwave component analyzer performs a calibration measurement utilizing the short single mode optical fiber as a calibration standard, as indicated by the numeral 224 shown in FIG. 3. Then, the user disconnects the short single mode optical fiber calibration standard from the lightwave component analyzer and connects the single mode optical fiber to be measured, as indicated by the numeral 226 shown in FIG. 3. The user next actuates a "AUTO TRAVEL TIME" key, which can be a dedicated instrument key or a firmware-generated menu and soft key displayed to the user, as indicated by the numeral 228 shown in FIG. 3. Then, the lightwave component analyzer measures and stores the travel time of light in the single mode optical fiber being measured so that its chromatic dispersion factor can be determined, as indicated by the numeral 230 shown in FIG. 3. The travel time determination method is resident in the commercially available HP 8703A lightwave component analyzer and does not form part of this invention.

After the lightwave component analyzer determines the travel time of light in the single mode optical fiber whose chromatic dispersion is to be determined, the user preferably disconnects the length of the single mode optical fiber whose chromatic dispersion is to be determined and preferably reconnects the calibration standard in the form of the short length of single mode optical fiber to the lightwave component analyzer, in accordance with the step 210 shown in FIG. 3. Then, the lightwave component analyzer performs a calibration measurement utilizing the short single mode optical fiber, which is followed by the steps 212, 214, 216, and 218 shown in FIG. 3 to produce a computation of the chromatic dispersion factor D for the fiber in ps/nm/km in accordance with expression (3), above.

Figure 4:
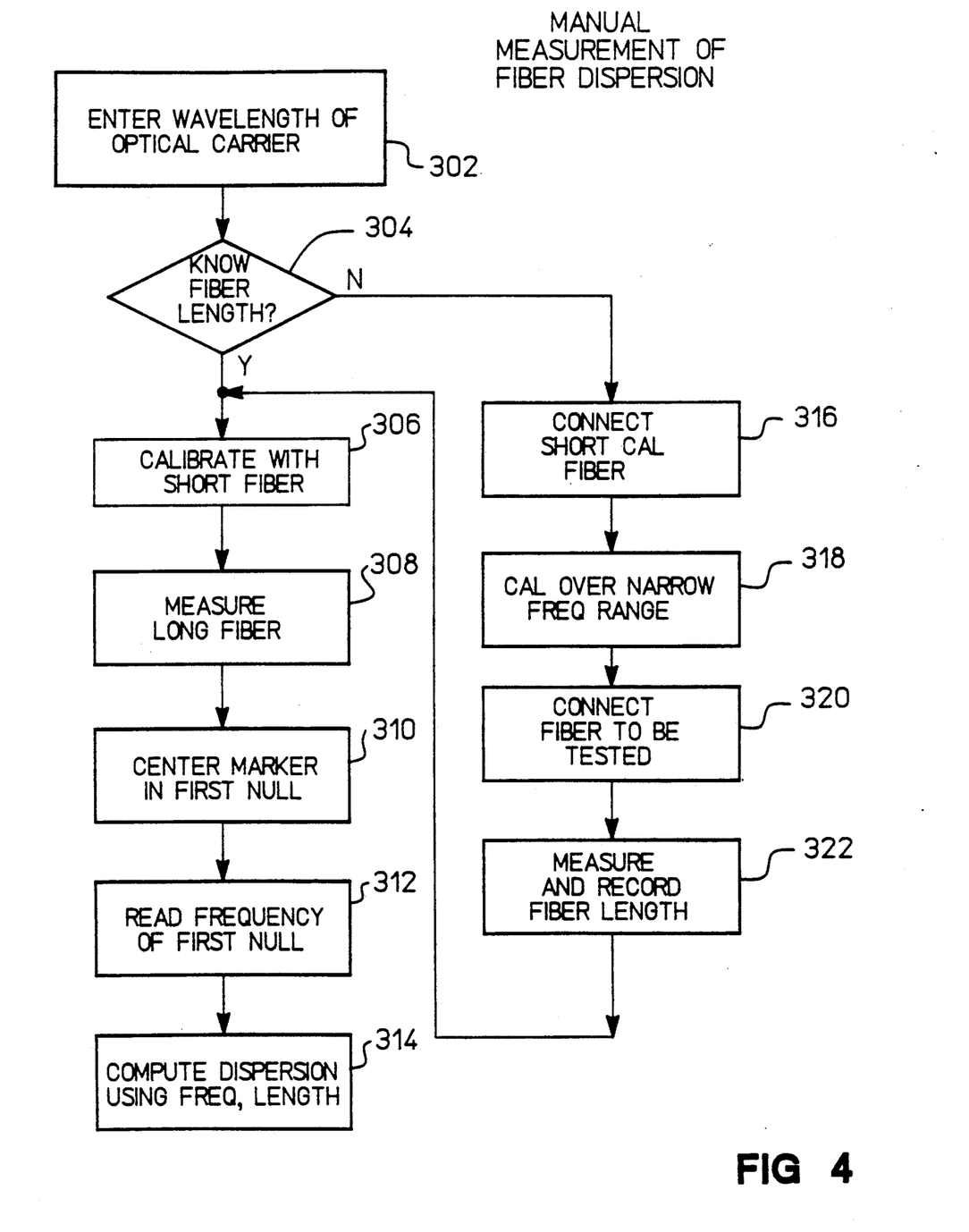
FIG. 4 is a flow chart of a modification of the embodiment of the method in accordance with the invention shown in the flow chart of FIG. 2 for determining chromatic dispersion in a single mode optical fiber using the fiber length.

One embodiment of the primarily manual chromatic dispersion method in accordance with the invention using expression (2), above, is shown in FIG. 4. As shown in FIG. 4, in the case of primarily manual chromatic dispersion determination based on expression (2), the user enters the known free-space wavelength, $\lambda_o$, of the optical signal produced by the optical source in meters, as indicated by the numeral 302 shown in FIG. 4. The user then determines whether or not he or she knows the length of the single mode optical fiber to be measured, as indicated by the numeral 304 shown in FIG. 4.

If the length of the single mode optical fiber is known, that is, the length has been previously measured or provided by the manufacturer of the fiber, the user preferably connects a calibration standard in the form of a short length of single mode optical fiber to the lightwave component analyzer, as indicated by the numeral 306 shown in FIG. 4, and the lightwave component analyzer performs a calibration measurement utilizing the short fiber. Then, the user disconnects the short single mode optical fiber calibration standard from the lightwave component analyzer and connects the single mode optical fiber to be measured, so that its chromatic dispersion factor can be determined, and the lightwave component analyzer is used to measure $F_m$, as indicated by the numeral 308 shown in FIG. 4.

Next, the user preferably centers a marker of the lightwave component analyzer in the first minimum, or null, observed on the AM frequency response characteristic of the single mode optical fiber displayed by the lightwave component analyzer, as indicated by the numeral 310 shown in FIG. 4. Then, the user reads the frequency of the first null, as indicated by the numeral 312 shown in FIG. 4, and enters the fiber length, as well as the frequency $F_m$. Finally, the user utilizes the lightwave component analyzer as a calculator to compute the chromatic dispersion factor D in ps/nm/km in accordance with expression (2), above, using 1) the speed of light in free space, c, resident in the memory of the lightwave component analyzer, 2) the entered free-space wavelength $\lambda_o$ of the optical carrier signal, 3) the entered length L of the single mode optical fiber, and 4) the measured modulating frequency $F_m$ at the minimum in the AM frequency response characteristic of the fiber, as indicated by the numeral 314 shown in FIG. 4.

If, on the other hand, the user does not know the length of the single mode optical fiber at step 304 shown in FIG. 4, the user preferably connects a calibration standard in the form of a short length of single mode optical fiber to the lightwave component analyzer, as indicated by the numeral 316 shown in FIG. 4. Next, the lightwave component analyzer performs a calibration measurement utilizing the short single mode optical fiber as a calibration standard over a frequency calibration selected by the user, as indicated by the numeral 318 shown in FIG. 4. Then, the user disconnects the short single mode optical fiber calibration standard from the lightwave component analyzer and connects the single mode optical fiber to be measured, as indicated by the numeral 320 shown in FIG. 4. The user next commands the lightwave component analyzer to measure and store the length of the single mode optical fiber being measured so that its chromatic dispersion factor can be determined, as indicated by the numeral 322 shown in FIG. 4. The length determination method is resident in the commercially available HP 8703A lightwave component analyzer and does not form part of this invention.

After the lightwave component analyzer determines the length of the single mode optical fiber whose chromatic dispersion is to be determined, the user preferably disconnects the length of the single mode optical fiber whose chromatic dispersion is to be determined and preferably reconnects the calibration standard in the form of the short length of single mode optical fiber to the lightwave component analyzer, in accordance with the step 306 shown in FIG. 4. Then, the lightwave component analyzer performs a calibration measurement utilizing the short fiber, which is followed by the steps 308, 310, 312, and 314 shown in FIG. 4 to produce a computation of the chromatic dispersion factor D for the fiber in ps/nm/km in accordance with expression (2), above.

Figure 5:
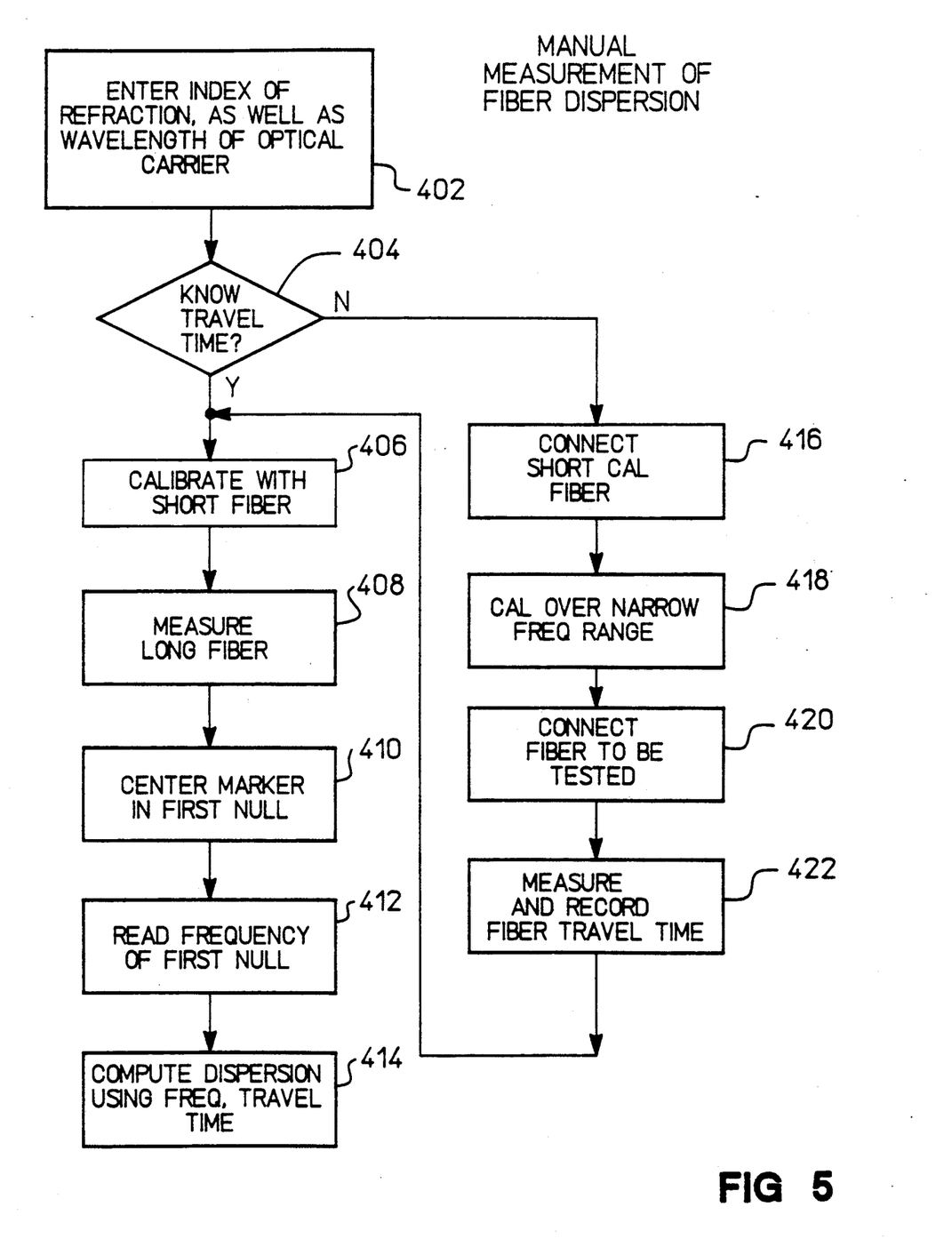
FIG. 5 is a flow chart of a modification of the embodiment of the method in accordance with the invention shown in the flow chart of FIG. 3 for determining chromatic dispersion in a single mode optical fiber using optical signal travel time in the fiber.

Another embodiment of a primarily manual chromatic dispersion method in accordance with the invention using expression (3), above, is shown in FIG. 5. As shown in FIG. 5, in the case of primarily manual chromatic dispersion determination based on expression (3), above, the user enters the known index of refraction of the single mode optical fiber at the frequency $F_o$ of the optical signal produced by the optical source, as well as the free-space wavelength, $\lambda_o$, of the optical signal produced by the optical source, as indicated by the numeral 402 shown in FIG. 5. The user then determines whether or not he or she knows the travel time of light in the single mode optical fiber, as indicated by the numeral 404 shown in FIG. 5.

If the travel time of light in the single mode optical fiber is known, that is, the travel time has been previously measured, the user preferably connects a calibration standard in the form of a short length of single mode optical fiber to the lightwave component analyzer, as indicated by the numeral 406 shown in FIG. 5, and the lightwave component analyzer performs a calibration measurement utilizing the short fiber. Then, the user disconnects the short single mode optical fiber calibration standard from the lightwave component analyzer and connects the single mode optical fiber to be measured, so that its chromatic dispersion factor can be determined, and the lightwave component analyzer is used to measure $F_m$, as indicated by the numeral 408 shown in FIG. 5.

Next, the user preferably centers a marker of the lightwave component analyzer in the first minimum, or null, observed on the AM frequency response characteristic of the single mode optical fiber displayed by the lightwave component analyzer, as indicated by the numeral 410 shown in FIG. 5. Then, the user reads the frequency of the first null, as indicated by the numeral 412 shown in FIG. 5, and enters the travel time, as well as the frequency $F_m$. Finally, the user utilizes the lightwave component analyzer as a calculator to compute the dispersion factor D in ps/nm/km in accordance with expression (3), above, using 1) the entered index of refraction n, 2) the free-space wavelength $\lambda_o$ of the optical carrier signal, 3) the entered travel time of light in the single mode optical fiber, and 4) the measured modulating frequency $F_m$ at the minimum in the AM frequency response characteristic of the fiber, as indicated by the numeral 414 shown in FIG. 5.

If, on the other hand, the user does not know the travel time of light in the single mode optical fiber at step 404 shown in FIG. 5, the user preferably connects a calibration standard in the form of a short length of single mode optical fiber to the lightwave component analyzer, as indicated by the numeral 416 shown in FIG. 5. Next, the lightwave component analyzer performs a calibration measurement utilizing the short single mode optical fiber as a calibration standard over a frequency calibration range selected by the user, as indicated by the numeral 418 shown in FIG. 5. Then, the user disconnects the short single mode optical fiber calibration standard from the lightwave component analyzer and connects the single mode optical fiber to be measured, as indicated by the numeral 420 shown in FIG. 5. The user next commands the lightwave component analyzer to measure and store the travel time of light in the single mode optical fiber being measured so that its chromatic dispersion factor can be determined, as indicated by the numeral 422 shown in FIG. 5. The travel time determination method is resident in the commercially available HP 8703A lightwave component analyzer and does not form part of this invention.

After the lightwave component analyzer determines the travel time of light in the single mode optical fiber whose chromatic dispersion is to be determined, the user preferably disconnects the length of the single mode optical fiber whose chromatic dispersion is to be determined and preferably reconnects the calibration standard in the form of the short length of single mode optical fiber to the lightwave component analyzer, in accordance with the step 406 shown in FIG. 5. Then, the lightwave component analyzer performs a calibration measurement utilizing the short single mode optical fiber, which is followed by the steps 408, 410, 412, and 414 shown in FIG. 5 to produce a computation of the chromatic dispersion factor D for the fiber in ps/nm/km in accordance with expression (3), above.

Figure 6:
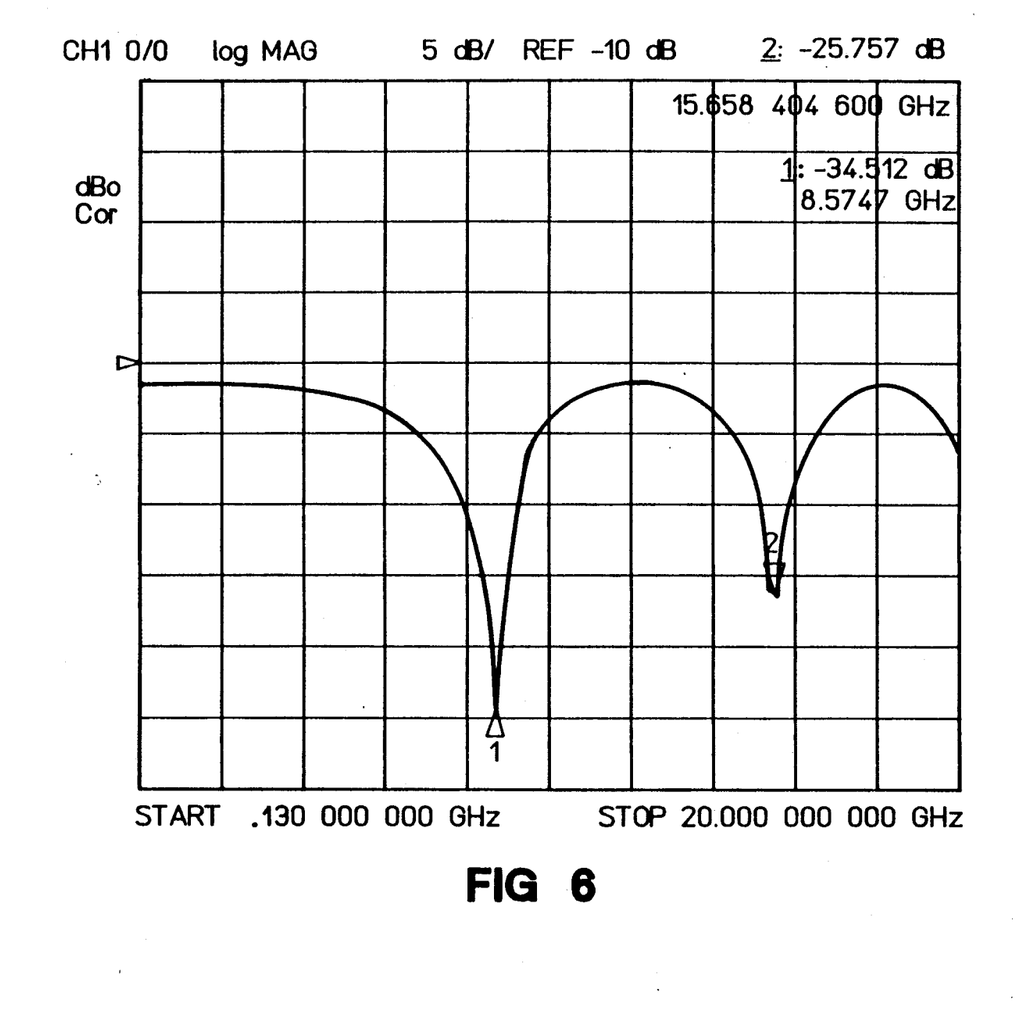
FIG. 6 illustrates the characteristic minima, or nulls, in the AM frequency response of a single mode optical fiber which exhibits chromatic dispersion, the frequencies at the minima, or nulls, being measured by a lightwave component analyzer for use in determining the chromatic dispersion factor for the fiber.

FIG. 6 illustrates the AM frequency response characteristic of a 43 kilometer length of single mode optical fiber which exhibits minima, or nulls, at $F_m$ equal to approximately 8.5747 GHz (first minimum, or null) and 15.6584046 GHz (second minimum, or null). The dispersion factor for this single mode optical fiber is therefore 19.7 ps/nm/km using expression (2) above, and this value is preferably displayed by the lightwave component analyzer.

Improvement in the accuracy of the chromatic dispersion measurements described above can be obtained by measuring the frequency $F_m$ of the minima, or nulls, twice, once with the optical modulator biased at quadrature on a positive slope and again with the modulator biased at quadrature on a negative slope, then preferably using the average of the measurements of the first minimum, or null, in expression (2) or expression (3), above. This cancels the effect of unwanted phase modulation.

The foregoing description is offered primarily for purposes of illustration. While a variety of embodiments has been disclosed, it will be readily apparent to those skilled in the art that numerous other modifications and variations not mentioned above can still be made without departing from the spirit and scope of the invention as claimed below.

What is claimed is:

1. A method for determining chromatic dispersion in single mode optical fiber, comprising the steps of:
   generating an optical carrier signal;
   providing one of the free-space wavelength and the frequency of the optical carrier signal to a lightwave component analyzer;
   connecting a single mode optical fiber, whose chromatic dispersion is to be determined, to the lightwave component analyzer;
   providing the length of the single mode optical fiber to the lightwave component analyzer;
   AM modulating the optical carrier signal to produce a modulated optical signal;
   applying the modulated optical signal to the single mode optical fiber;
   measuring the modulating frequency at minima of an AM frequency response characteristic of the single mode optical fiber in response to the modulated optical signal with the lightwave component analyzer;
   ascertaining the modulating frequency at a predetermined minimum in the AM frequency response characteristic of the single mode optical fiber; and
   using the one of the free-space wavelength and the frequency of the optical carrier signal, the single mode optical fiber length, and the modulating frequency at the predetermined minimum in the AM frequency response measurement for computing a chromatic dispersion factor by means of the lightwave component analyzer.

2. The method of claim 1 wherein the step of providing the length of the single mode optical fiber to the lightwave component analyzer comprises measuring the length of the single mode optical fiber with the lightwave component analyzer.

3. The method of claim 1 wherein the step of ascertaining the modulating frequency at a predetermined minimum in the AM frequency response characteristic of the single mode optical fiber comprises positioning a marker of the lightwave component analyzer at the predetermined minimum.

4. The method of claim 1, further comprising the step of providing the speed of light to the lightwave component analyzer, wherein the modulating frequency at a first minimum in the AM frequency response characteristic of the single mode optical fiber is ascertained and a chromatic dispersion factor, D, is computed by means of the lightwave component analyzer according to the expression:

$$D_{N=0} = \frac{c}{2L\lambda_o^2 F_m^2}$$

where D is the dispersion factor in s/m/m; $F_o$ is the frequency of the optical carrier signal in Hz; $F_m$ is the measured modulating frequency at the first minimum in Hz; c is the speed of light in free space in m/s; L is the length of the single mode optical fiber in m; and $\lambda_o$ is the free space wavelength of the optical carrier signal in meters and is equal to $c/F_o$.

5. The method of claim 1 wherein the step of ascertaining the modulating frequency at the predetermined minimum in the AM frequency response characteristic of the single mode optical fiber comprises the steps of:
   measuring the frequency of the minima twice, once with an optical modulator that modulates the optical carrier signal biased at quadrature on a positive slope and again with the optical modulator biased at quadrature on a negative slope; and
   using the average of the two minima measurements at the predetermined minimum in the AM frequency response characteristic of the single mode optical fiber as the modulating frequency to compute the chromatic dispersion factor;
   thereby canceling the effect of unwanted phase modulation.

6. The method of claim 1 wherein prior to the step of connecting the single mode optical fiber to the lightwave component analyzer, further comprising the steps of:
   connecting a calibration standard in the form of a short length of single mode optical fiber to the lightwave component analyzer;
   performing a calibration measurement utilizing the short single mode optical fiber calibration standard by means of the lightwave component analyzer; and
   disconnecting the short single mode optical fiber calibration standard from the lightwave component analyzer.

7. The method of claim 2 wherein prior to the step of connecting the single mode optical fiber to the lightwave component analyzer, further comprising the steps of:
   initially connecting a calibration standard in the form of a short length of single mode optical fiber to the lightwave component analyzer;
   performing a calibration measurement utilizing the short single mode optical fiber calibration standard by means of the lightwave component analyzer; and
   disconnecting the short single mode optical fiber calibration standard from the lightwave component analyzer; and wherein prior to the step of measuring the modulating frequency at minima of the AM frequency response characteristic of the single mode optical fiber in response to the modulated optical signal with the lightwave component analyzer, further comprising the steps of:
   disconnecting the single mode optical fiber from the lightwave component analyzer;
   connecting the calibration standard int he form of the short length of single mode optical fiber to the lightwave component analyzer;
   performing a calibration measurement utilizing the short single mode optical fiber calibration standard by means of the lightwave component analyzer;
   disconnecting the short single mode optical fiber calibration standard from the lightwave component analyzer; and
   reconnecting the single mode optical fiber, whose chromatic dispersion is to be determined, to the lightwave component analyzer.

8. The method of claim 7 wherein prior to initially connecting the calibration standard in the form of the short length of single mode optical fiber to the lightwave component analyzer, further comprising the step of:

providing an estimate of the length of the single mode optical fiber, whose chromatic dispersion is to be determined, to enable the lightwave component analyzer to select an appropriate frequency range for calibration.

9. The method of claim 1, further comprising the step of displaying the AM frequency response characteristic of the single mode optical fiber by means of the lightwave component analyzer so that the minima can be observed.

10. A method for determining chromatic dispersion in single mode optical fiber, comprising the steps of:

generating an optical carrier signal;

providing the index of refraction of a single mode optical fiber, whose chromatic dispersion is to be determined, to a lightwave component analyzer;

connecting the single mode optical fiber to the lightwave component analyzer;

providing the travel time of the optical carrier signal in the single mode optical fiber to the lightwave component analyzer;

AM modulating the optical carrier signal to produce a modulated optical signal;

applying the modulated optical signal to the single mode optical fiber;

measuring the modulating frequency at minima of an AM frequency response characteristic of the single mode optical fiber in response to the modulated optical signal with the lightwave component analyzer;

ascertaining the modulating frequency at a predetermined minimum in the AM frequency response characteristic of the single mode optical fiber; and using the index of refraction, the travel time in the single mode optical fiber, and the modulating frequency at the predetermined minimum in the AM frequency response measurement for computing a chromatic dispersion factor by means of the lightwave component analyzer.

11. The method of claim 10 wherein the step of providing the travel time of the optical carrier signal in the single mode optical fiber to the lightwave component analyzer comprises measuring the travel time of the optical carrier signal in the single mode optical fiber with the lightwave component analyzer.

12. The method of claim 10 wherein the step of ascertaining the modulating frequency at a predetermined minimum in the AM frequency response characteristic of the single mode optical fiber comprises positioning a marker of the lightwave component analyzer at the predetermined minimum.

13. The method of claim 10 wherein the modulating frequency at a first minimum in the AM frequency response characteristic of the single mode optical fiber is ascertained and a chromatic dispersion factor, D, is computed by means of the lightwave component analyzer according to the expression:

$$D_{N=0} = \frac{n}{2\tau_0^2 F_m^2}$$

where D is the dispersion factor in s/m/m; n is the index of refraction of the glass single mode optical fiber core at the frequency $F_o$ of the optical carrier signal, which is dimensionless; $\tau_o$ is the time required for light at the frequency $F_o$ to travel the length of the single mode optical fiber in seconds; and $F_m$ is the measured modulating frequency at the first minimum in Hz.

14. The method of claim 10 wherein the step of ascertaining the modulating frequency at the predetermined minimum in the AM frequency response characteristic of the single mode optical fiber comprises the steps of:

measuring the frequency of the minima twice, once with an optical modulator that modulates the optical carrier signal biased at quadrature on a positive slope and again with the optical modulator biased at quadrature on a negative slope; and using the average of the two minima measurements at the predetermined minimum in the AM frequency response characteristic of the single mode optical fiber as the modulating frequency to compute the chromatic dispersion factor;

thereby canceling the effect of unwanted phase modulation.

15. The method of claim 10 wherein prior to the step of connecting the single mode optical fiber to the lightwave component analyzer, further comprising the steps of:

connecting a calibration standard in the form of a short length of single mode optical fiber to the lightwave component analyzer;

performing a calibration measurement utilizing the short single mode optical fiber calibration standard by means of the lightwave component analyzer; and disconnecting the short single mode optical fiber calibration standard from the lightwave component analyzer.

16. The method of claim 11 wherein prior to the step of connecting the single mode optical fiber to the lightwave component analyzer, further comprising the steps of:

initially connecting a calibration standard in the form of a short length of single mode optical fiber to the lightwave component analyzer;

performing a calibration measurement utilizing the short single mode optical fiber calibration standard by means of the lightwave component analyzer; and disconnecting the short single mode optical fiber calibration standard from the lightwave component analyzer; and wherein prior to the step of measuring the modulating frequency at minima of the AM frequency response characteristic of the single mode optical fiber in response to the modulated optical signal with the lightwave component analyzer, further comprising the steps of:

disconnecting the single mode optical fiber from the lightwave component analyzer;

connecting the calibration standard in the form of the short length of single mode optical fiber to the lightwave component analyzer;

performing a calibration measurement utilizing the short single mode optical fiber calibration standard by means of the lightwave component analyzer;

disconnecting the short single mode optical fiber calibration standard from the lightwave component analyzer; and reconnecting the single mode optical fiber, whose chromatic dispersion is to be determined, to the lightwave component analyzer.

17. The method of claim 16 wherein prior to initially connecting the calibration standard in the form of the short length of single mode optical fiber to the lightwave component analyzer, further comprising the step of:

providing an estimate of the length of the single mode optical fiber, whose chromatic dispersion is to be determined, to enable the lightwave component analyzer to select an appropriate frequency range for calibration.

18. The method of claim 10, further comprising the step of displaying the AM frequency response characteristic of the single mode optical fiber by means of the lightwave component analyzer so that the minima can be observed.

19. A method for determining chromatic dispersion in single mode optical fiber, comprising the steps of:

generating an optical carrier signal;

connecting a single mode optical fiber, whose chromatic dispersion is to be determined, to a lightwave component analyzer;

providing a) one of the free-space wavelength and the frequency of the optical carrier signal, as well as the length of the single mode optical fiber, and, alternatively, b) the index of refraction of the single mode optical fiber and the travel time of the optical carrier signal in the single mode optical fiber to the lightwave component analyzer;

AM modulating the optical carrier signal to produce a modulated optical signal;

applying the modulated optical signal to the single mode optical fiber;

measuring the modulating frequency at minima of an AM frequency response characteristic of the single mode optical fiber in response to the modulated optical signal with the lightwave component analyzer;

ascertaining the modulating frequency at a predetermined minimum in the AM frequency response characteristic of the single mode optical fiber; and using the modulating frequency at the predetermined minimum in the AM frequency response measurement and a) the one of the free-space wavelength and the frequency of the optical carrier signal, as well as the single mode optical fiber length, and, alternatively, b) the index of refraction and the travel time in the single mode optical fiber for computing a chromatic dispersion factor by means of the lightwave component analyzer.

20. The method of claim 19 wherein the step of ascertaining the modulating frequency at the predetermined minimum in the AM frequency response characteristic of the single mode optical fiber comprises the steps of:

measuring the frequency of the minima twice, once with an optical modulator that modulates the optical carrier signal biased at quadrature on a positive slope and again with the optical modulator biased at quadrature on a negative slope; and using the average of the two minima measurements at the predetermined minimum in the AM frequency response characteristic of the single mode optical fiber as the modulating frequency to compute the chromatic dispersion factor;

thereby canceling the effect of unwanted phase modulation.

* * * * *